United States Patent [19]
Belknap

[11] Patent Number: 5,911,726
[45] Date of Patent: Jun. 15, 1999

[54] SURGICAL MESH STABILIZER

[76] Inventor: John C. Belknap, 1740 Amherst St., Buffalo, N.Y. 14214

[21] Appl. No.: 09/010,721

[22] Filed: Jan. 22, 1998

[51] Int. Cl.⁶ .................................................. A61B 17/00
[52] U.S. Cl. .............................................................. 606/144
[58] Field of Search .................................... 606/144, 148, 606/151, 142, 167, 171, 184, 185, 139, 169, 222–227

[56] References Cited

U.S. PATENT DOCUMENTS

| | | |
|---|---|---|
| 4,917,100 | 4/1990 | Nottke . |
| 5,147,373 | 9/1992 | Ferzli ...................... 606/144 |
| 5,281,237 | 1/1994 | Gimpelson ............... 606/144 |
| 5,562,685 | 10/1996 | Mollenauer et al. ..................... 606/144 |
| 5,573,542 | 11/1996 | Stevens ..................................... 606/144 |

*Primary Examiner*—Michael Buiz
*Assistant Examiner*—Vikki Trinh
*Attorney, Agent, or Firm*—Joseph P. Gastel

[57] ABSTRACT

A surgical mesh stabilizer including a cannula having a proximal cannula end and a distal cannula end, a stylet having a proximal stylet end and a distal stylet end, a hook on the distal stylet end, the stylet being slidably mounted in the cannula and movable between a remote position wherein the proximal stylet end is remote from the proximal cannula end and the hook is sheathed within the distal cannula end and a near position wherein the proximal stylet end is near the proximal cannula end and the hook is unsheathed from the distal cannula end, a disc slidably mounted on the distal cannula end, a hub fixedly mounted on the proximal cannula end and a spring extending between the hub and the disc.

15 Claims, 4 Drawing Sheets

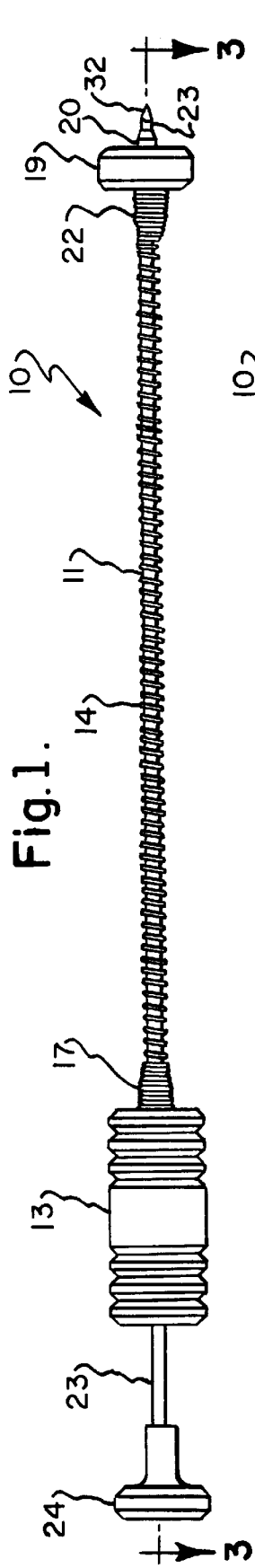
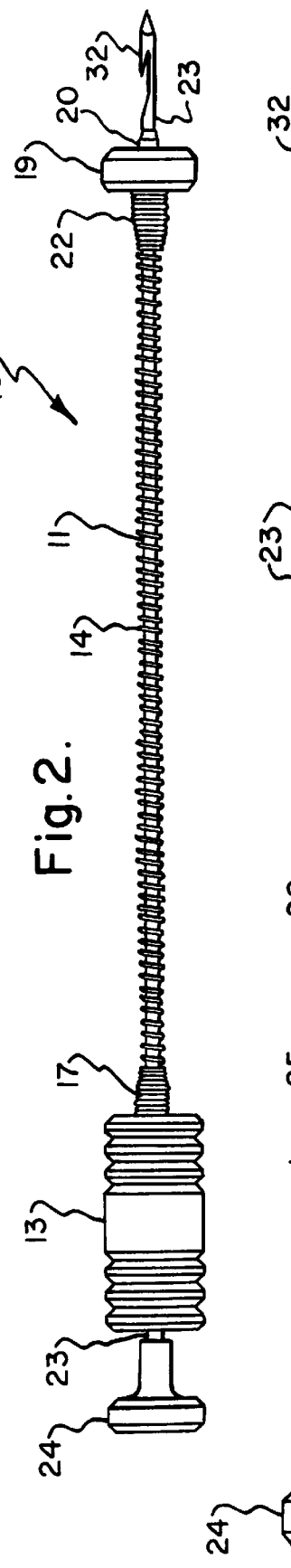
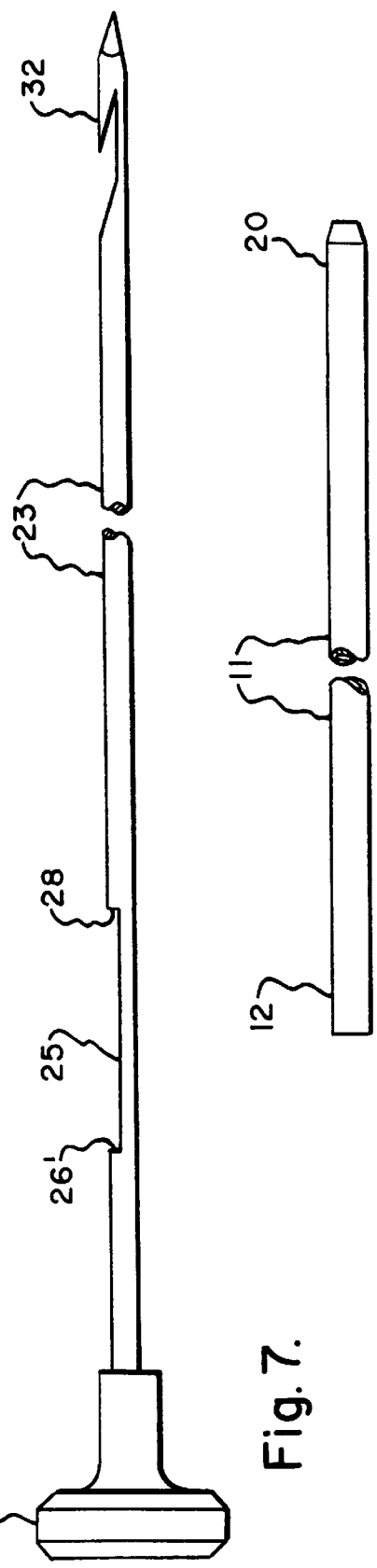
Fig.1.
Fig.2.
Fig. 7.
Fig. 8.

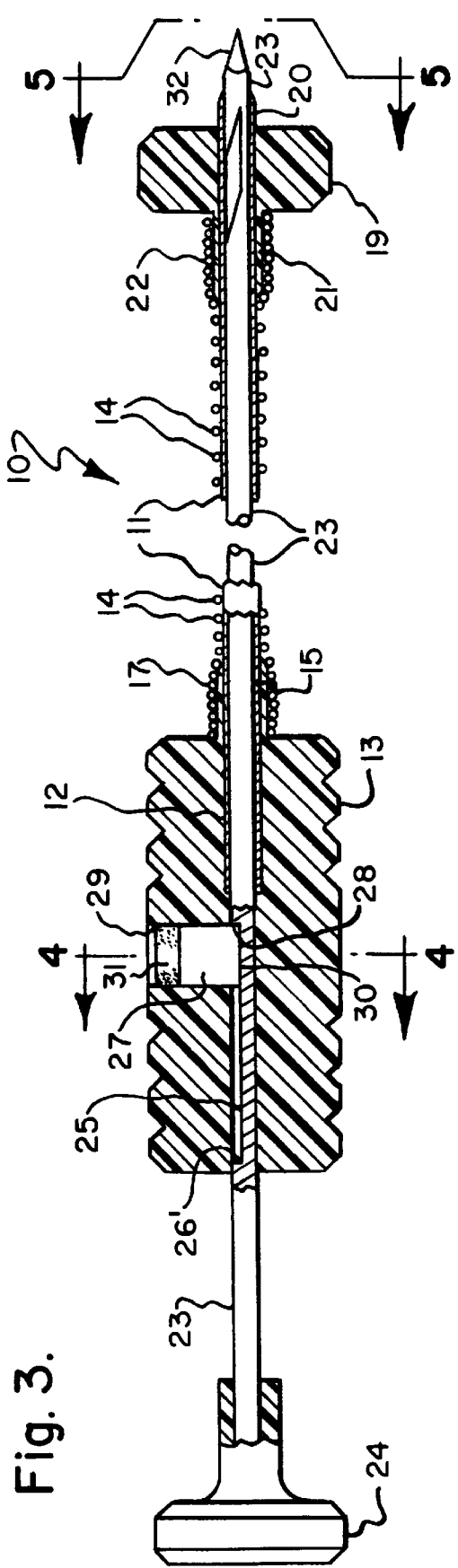
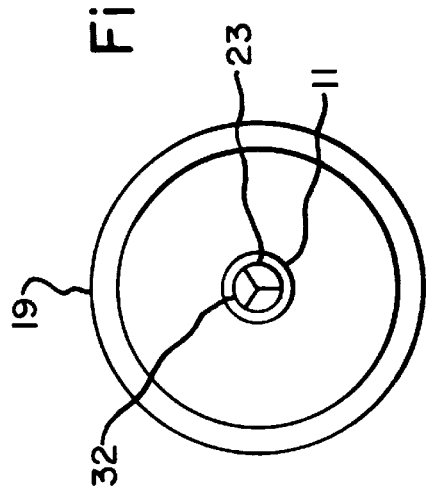
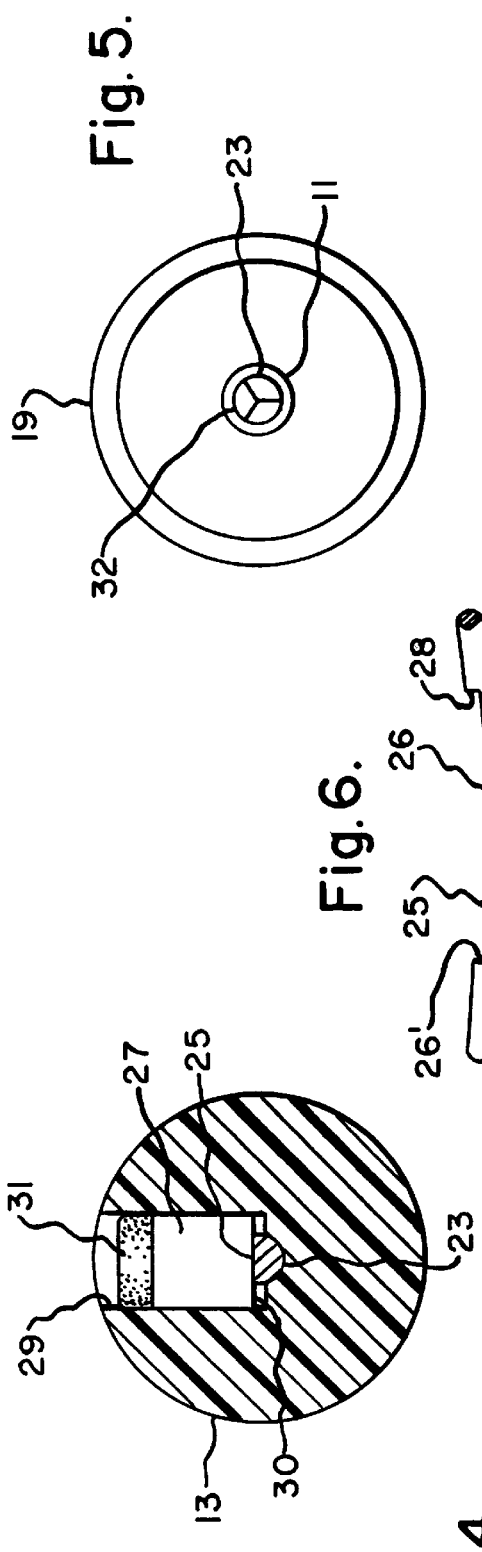
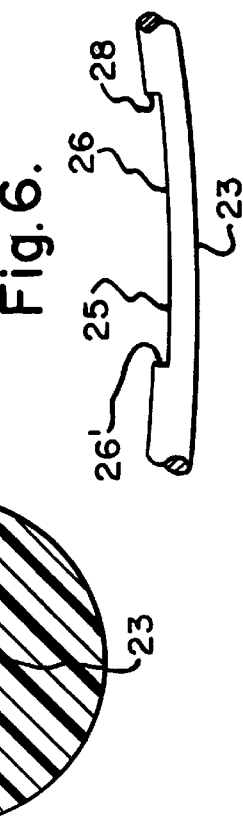
Fig. 3.
Fig. 5.
Fig. 6.
Fig. 4.

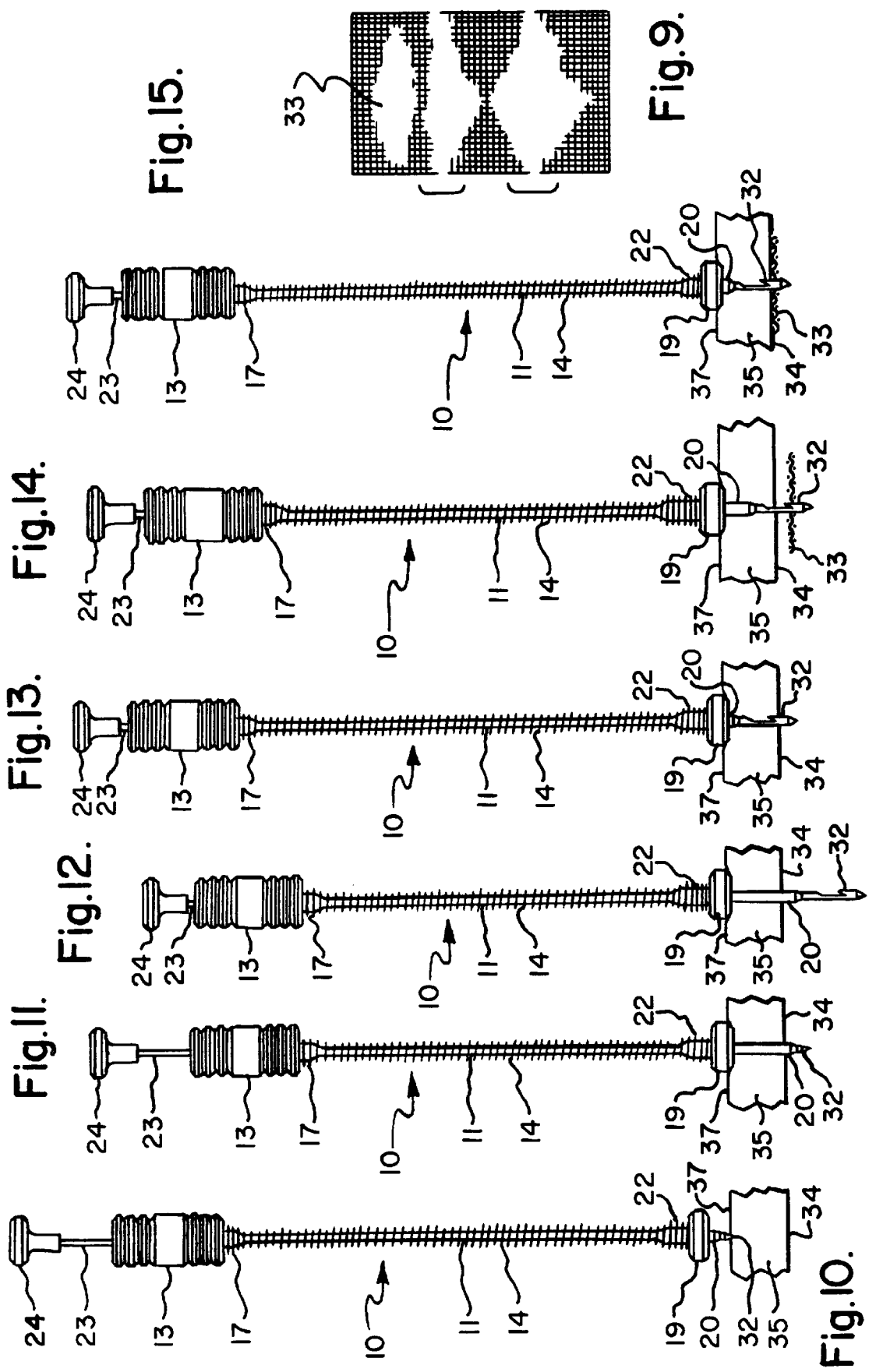

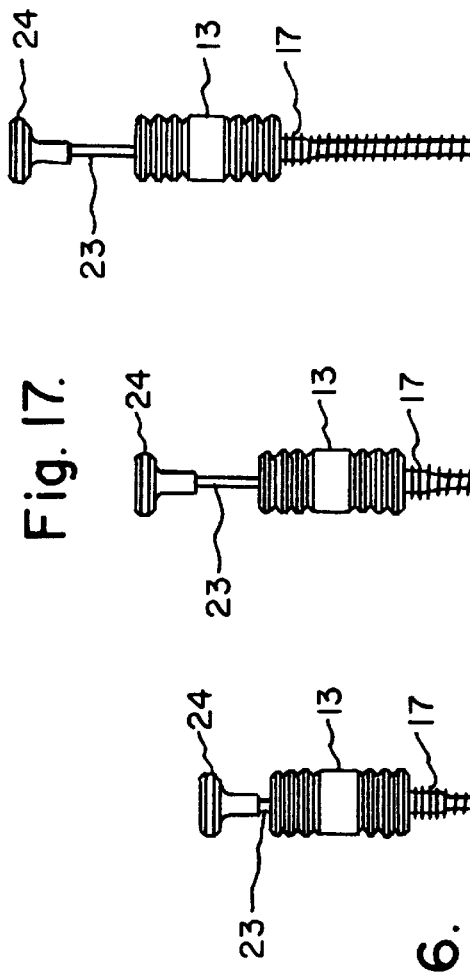
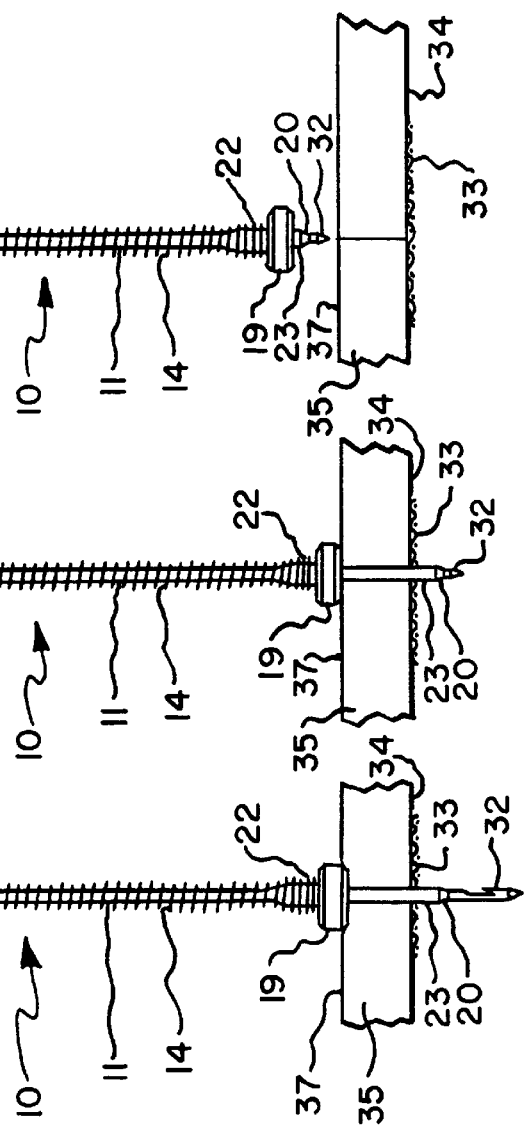

5,911,726

SURGICAL MESH STABILIZER

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The present invention relates to a surgical mesh stabilizer for securing a mesh to the inner surface of an abdominal wall for subsequent surgical attachment thereto during hernia repair and thereafter withdrawing the surgical mesh stabilizer from the abdominal wall.

By way of background, in hernia repair surgery, a 4×6 inch plastic mesh is moved to the proper site along the inner surface of the abdominal wall by conventional laparoscopic surgical procedures. Thereafter, the mesh has to be stabilized in position against the inner surface of the abdominal wall so that it can be firmly attached in position, usually by means of staples. In the past, laparoscopic tools were used to move the plastic mesh to the proper position. However, there was no efficient way to secure it in such position while it was being permanently stapled to the inner surface of the abdominal wall.

BRIEF SUMMARY OF THE INVENTION

It is the primary object of the present invention to provide a surgical mesh stabilizer which can be used to positively secure a mesh to the inner surface of an abdominal wall preparatory to its being stapled thereto.

Another object of the present invention is to provide a surgical mesh stabilizer which will automatically adjust its hooking function to different thicknesses of abdominal walls.

A further object of the present invention is to provide a surgical mesh stabilizer which requires relatively few manipulative steps on the part of a surgeon to bring a hook into engagement with the inner surface of an abdominal wall.

A still further object of the present invention is to provide a surgical mesh stabilizer which can be withdrawn from a hooking position relative to the internal surface of an abdominal wall in an extremely efficient manner with relatively few manipulative steps.

Yet another object of the present invention is to provide a surgical mesh stabilizer which has relatively few simple parts and which can function in a highly efficient and reliable manner. Other objects and attendant advantages of the present invention will readily be perceived hereafter.

The present invention relates to a surgical mesh stabilizer comprising a cannula having a proximal cannula end and a distal cannula end, a stylet having a proximal stylet end and a distal stylet end, a hook on said distal stylet end, said stylet being slidably mounted in said cannula and movable between a remote position wherein said proximal stylet end is remote from said proximal cannula end and said hook is retracted within said distal cannula end and a near position wherein said proximal stylet end is near said proximal cannula end and said hook is extended from said distal cannula end, and a disc slidably mounted on said distal cannula end. In its more specific aspect the surgical mesh stabilizer includes a spring biasing said disc toward said distal cannula end.

The various aspects of the present invention will be more fully understood when the following portions of the specification are read in conjunction with the accompanying drawings wherein:

BRIEF DESCRIPTION OF THE SEVERAL VIEWS OF THE DRAWING

FIG. 1 is a side elevational view of the surgical mesh stabilizer of the present invention wherein the various parts are in a position wherein the hook end of the stylet is retracted within the cannula;

FIG. 2 is a side elevational view of the surgical mesh stabilizer of FIG. 1 showing the relationship of the various parts when the hook end is extended from the cannula;

FIG. 3 is a fragmentary cross sectional view taken substantially along line 3—3 of FIG. 1;

FIG. 4 is a cross sectional view taken substantially along line 4—4 of FIG. 3;

FIG. 5 is an end elevational view taken substantially in the direction of arrows 5—5 of FIG. 3;

FIG. 6 is a fragmentary side elevational view of a portion of the stylet which is slightly bent;

FIG. 7 is a fragmentary side elevational view of the stylet;

FIG. 8 is a fragmentary cross sectional view of the cannula;

FIG. 9 is a reduced fragmentary plan view of the mesh which is stabilized by the surgical mesh stabilizer of FIG. 1;

FIG. 10 is a side elevational view of the surgical mesh stabilizer as it starts to enter the abdominal wall of a patient;

FIG. 11 is a side elevational view of the surgical mesh stabilizer showing the position of its various parts after the cannula has completely penetrated the abdominal wall while the hook end of the stylet is still retracted within the cannula;

FIG. 12 is a side elevational view showing the relationship of the various parts after the hook end of the stylet has been extended while the cannula remains in the position of FIG. 11;

FIG. 13 is a side elevational view of the device showing the relationship of the various parts after the surgical mesh stabilizer has been released by the surgeon and the spring retracts the cannula from its extended position of FIG. 12 and causes the hook end of the stylet to engage the inner surface of the abdominal wall;

FIG. 14 is a side elevational view of the surgical mesh stabilizer after the hook end of the stylet is pushed away from the internal surface of the abdominal wall and through the mesh of FIG. 9;

FIG. 15 is a side elevational view of a surgical mesh stabilizer after it has been released by the surgeon so that the spring expands to pull the mesh up against the inner surface of the abdominal wall;

FIG. 16 is a side elevational view of the surgical mesh stabilizer which has been manually moved to a position wherein the cannula is pushed through the mesh while the hook end of the stylet is in an extended position preparatory to removing the surgical mesh stabilizer from the abdominal wall;

FIG. 17 is a side elevational view of the surgical mesh stabilizer with the parts in position wherein the hook end of the stylet has been retracted into the cannula so that the surgical mesh stabilizer can pass through the mesh and outwardly through the abdominal wall without hooking; and FIG. 18 is a view showing the parts in their relative positions after the surgical mesh stabilizer has been removed from the abdominal wall.

DETAILED DESCRIPTION OF THE INVENTION

The surgical mesh stabilizer 10 of the present invention includes a cannula 11 (FIGS. 1, 3 and 8) having its proximal end 12 insert molded into one end of hub 13 which is fabricated of suitable moldable plastic. A coil spring 14 has one end mounted on boss 15 (FIG. 3) which is an integral molded part of hub 13. The end 17 of spring 14 is stretched so that it will exert a compressive force on boss 15 to retain spring 14 in assembled relationship with boss 15. A disc 19 is slidably mounted on the distal end 20 of cannula 11. Disc 19 is fabricated of plastic and includes an integrally molded boss 21 (FIG. 3) onto which the distal end 22 of spring 14 is stretched. The compressive force of spring end 22 on boss 21 maintains the attachment between spring 14 and disc 19.

A stylet 23 (FIGS. 1, 3 and 7) includes a proximal end having a plastic cap 24 insert-molded thereon. The stylet 23 includes a flat 25 (FIGS. 3 and 6) which is located within hub 13. A pin 27 is located in bore 29 of hub 13 and has its inner end 30 located at flat 25. A layer 31 of epoxy retains pin 27 in position. There is a sliding connection between the inner end 30 of pin 27 and flat 25. The limits of movement between stylet 23 and hub 13 are defined by shoulders 26' and 28 (FIG. 6) which engage pin 27. The flat 25 is fabricated with a very slight concave bend, as shown at 26 in FIG. 6, to provide a friction-fit with the inside of hub 13 and the end 12 of cannula 11 to thereby retain the stylet to any position in which it has been manually moved within hub 13.

The distal end of stylet 23 is formed into a hook 32 which is either retracted within the distal end 20 of cannula 11, as shown in FIGS. 1 and 3 when cap 24 is remote from hub 13, or extended from the distal end 20 of cannula 14, as shown in FIG. 2, when the cap 24 of the stylet 23 is moved to the position shown in FIG. 2 wherein it is in a near position relative to hub 13. At the near position, shoulder 26' engages pin 27, and at the remote position, shoulder 28 engages pin 27.

The function of the surgical mesh stabilizer 10 is to hook onto a plastic mesh 33 (FIG. 9) having a size of approximately 4×6 inches, which is utilized in hernia repair, and retain the mesh firmly in position against the inner side of the abdominal wall while the mesh is being stapled into its retained position. Thereafter, the surgical mesh stabilizer 10 is withdrawn from the abdominal wall. The placement, manipulation and removal of the stabilizer 10 is done under direct laparoscopic vision.

The procedure for hooking the mesh 33 against the inner surface 34 of abdominal wall 35 is depicted in FIGS. 10–15. In FIG. 10 the surgical mesh stabilizer 10 is shown with its various parts in the position in which they are placed as the abdominal wall piercing is initiated. At this time the hook 32 of the stylet 23 is retracted within the cannula end 20, and cap 24 is in a remote position away from hub 13 wherein shoulder 28 engages pin 27. Additionally the spring 14 is in its fully extended position so that disc 19 assumes the position of FIG. 10.

The next step in penetrating abdominal wall 35 is to digitally grasp hub 13 and push the cannula end 20 with hook end 23 retracted therein into the outer surface 37 of the abdominal wall 35. As the distal cannula end 20 penetrates the abdominal wall, a position will be reached where sliding disc 19 will engage the outer surface 37 of the abdominal wall. Continued movement of the distal end 20 through the abdominal wall while sliding disc 19 is against the outer surface 37 is continued until the cannula end 20 extends outwardly beyond the inner surface 34 of wall 35. This will result in spring 14 being compressed to the condition shown in FIG. 11 from its extended position of FIG. 10.

After the distal end 20 has reached its position of FIG. 11 wherein it extends beyond the inner surface 34 of abdominal wall 35, the cap 24 is moved toward hub 13 to the position of FIG. 12, and thus the hook 32 will be moved to its extended position shown in FIGS. 2 and 12. At this time, because of the bend 26 at the flat 25 of stylet 23, the stylet will be retained in a position wherein stylet shoulder 26' engages pin 27. Thereafter, both the hub 13 and cap 24 are digitally released, and the spring 14 will expand to the position of FIG. 13 from the position of FIG. 12 and in so doing will pull the distal end 20 of cannula 23 and the hook 32 of the stylet to the position of FIG. 13 wherein the hook 32 hooks into the inner surface 34 of the abdominal wall. The amount that distal end 20 of cannula 11 extends outwardly from sliding disc 19 when spring 14 is in its fully extended position should be less than the thickness of the abdominal wall so that when the spring biases the sliding disc against the abdominal wall and the cannula end 32 is retracted into the wall 35 while the hook 32 is extended, the latter will hook into the inner surface of the abdominal wall.

The next step in the procedure is to hook mesh 33 and bring it against the inner surface 34 of the abdominal wall. This is achieved by locating mesh 33 in its desired position relative to hook 32 by conventional laparoscopic surgical procedures and thereafter digitally pushing hub 13 while cap 24 is retained in the position of FIGS. 13 and 14 toward the abdominal wall 35 so that the hook 32 passes through mesh 33 and hooks onto it (FIG. 14). A laparoscopic grasping tool (not shown) is used to hold the mesh in position while pushing hook 32 through mesh 33. At this time spring 14 will be compressed to its position of FIG. 14 from its position of FIG. 13. Thereafter, hub 13 is released while cap 24 is in the position of FIG. 14, and spring 14 will expand to the position of FIG. 15 from its position of FIG. 14 to thereby bring mesh 33 into engagement with the inner surface 34 of abdominal wall 35. The hooking procedure can be repeated with additional surgical mesh stabilizers 10 the desired number of times to thereby positively locate and hold the mesh 33 up against the inner surface 34 of abdominal wall 35 with a plurality of surgical mesh stabilizers 10. Thereafter, the proper surgical stapling procedures are followed to attach the mesh to the inner surface of abdominal wall 35.

After the mesh has been attached to the inner surface 34 of the abdominal wall by stapling, the surgical mesh stabilizer 10 is withdrawn as depicted in FIGS. 16–18. The first step in the withdrawal process is to push hub 13 and cap 24 in their positions of FIGS. 15 and 16 toward the abdominal wall 35 to thereby push the distal end 20 of the cannula through the stapled mesh 33 while hook 32 is still in its extended position. This movement will cause spring 14 to be compressed from its position of FIG. 15 to its position of FIG. 16. The fact that there is a binding fit between the stylet and the hub because of the bend 26 at flat 25 when the cap 24 and hub 13 are in the position of FIG. 10, resists movement of cap 24 away from hub 13. After the cannula end 20 has been moved to the position of FIG. 16, the cap 24 is moved outwardly away from hub 13 to the position of FIG. 17, thereby retracting the hook 32 into cannula end 20. The next step is to pull hub 13 with cap 24 in the position of FIG. 12 outwardly away from abdominal wall 35 while the hook end 32 is sheathed within cannula end 20.

From the foregoing description, it will readily be appreciated that the spring 14 performs a modulating function in that it will cause the hook device 10 to be automatically operative with different thicknesses of abdominal walls. More specifically, regardless of the thickness of the abdominal wall, the spring 14 will always retract the hook 32 and the cannula 11 to their positions of FIG. 13 from their positions of FIG. 12. Also, it will be appreciated that the proximal end of spring 14 may be attached directly to cannula 11 in spaced relationship to hub 13 provided that it provides the proper spring force and stroke to effect the modulating function.

While preferred embodiments of the present invention have been disclosed, it will be appreciated that it is not limited thereto but may be otherwise embodied within the scope of the following claims.

I claim:

1. A surgical mesh stabilizer comprising a cannula having a proximal cannula end and a distal cannula end, a stylet having a proximal stylet end and a distal stylet end, a hook on said distal stylet end, said stylet being slidably mounted in said cannula and movable between a remote position wherein said proximal stylet end is remote from said proximal cannula end and said hook is sheathed within said distal cannula end and a near position wherein said proximal stylet end is near said proximal cannula end and said hook is unsheathed from said distal cannula end, and a disc slidably mounted on said distal cannula end.

2. A surgical mesh stabilizer as set forth in claim 1 including a spring biasing said disc toward said distal cannula end.

3. A surgical mesh stabilizer as set forth in claim 2 including a hub fixedly mounted on said cannula on the opposite side of said spring from said disc.

4. A surgical mesh stabilizer as set forth in claim 3 wherein said spring engages said hub.

5. A surgical mesh stabilizer as set forth in claim 1 including a cap on said proximal stylet end.

6. A surgical mesh stabilizer as set forth in claim 5 including a spring biasing said disc toward said distal cannula end.

7. A surgical mesh stabilizer as set forth in claim 6 including a hub fixedly mounted on said cannula on the opposite side of said spring from said disc.

8. A surgical mesh stabilizer as set forth in claim 7 wherein said spring engages said hub.

9. A surgical mesh stabilizer as set forth in claim 1 wherein said distal cannula end includes an extreme outer portion which extends outwardly beyond said disc.

10. A surgical mesh stabilizer as set forth in claim 9 including a spring biasing said disc toward said distal cannula end.

11. A surgical mesh stabilizer as set forth in claim 10 including a hub fixedly mounted on said cannula on the opposite side of said spring from said disc.

12. A surgical mesh stabilizer as set forth in claim 11 wherein said spring engages said hub.

13. A surgical mesh stabilizer as set forth in claim 12 including a cap on said proximal stylet end.

14. A surgical mesh stabilizer as set forth in claim 1 including a cap on said proximal stylet end, and a hub on said proximal cannula end.

15. A surgical mesh stabilizer as set forth in claim 14 wherein said distal cannula end includes an extreme outer portion which extends outwardly beyond said disc.

* * * * *